US00PP26770P3

(12) United States Plant Patent
Maillard et al.

(10) Patent No.: US PP26,770 P3
(45) Date of Patent: May 31, 2016

(54) NECTARINE TREE NAMED 'NECTAKING'

(50) Latin Name: ***Prunus persica* (L.) Batsch var. *nucipersica***
Varietal Denomination: NECTAKING

(71) Applicant: AGRO SELECTIONS FRUITS, Elne (FR)

(72) Inventors: Arsene Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 131 days.

(21) Appl. No.: 13/999,808

(22) Filed: Mar. 24, 2014

(65) Prior Publication Data

US 2015/0271968 P1 Sep. 24, 2015

(51) Int. Cl.
*A01H 5/00* (2006.01)

(52) U.S. Cl.
USPC ..... Plt./190

(58) Field of Classification Search
USPC ..... Plt./190
See application file for complete search history.

(56) References Cited

PUBLICATIONS

PLUTO Plant Variety database Jul. 22, 2015. p. 1.*
Redacted delivery estimate from Euro Pépinières to Bonnet dated Aug. 19, 2015; with English machine translation (3 pages).
Redacted invoice from ASF to Bonnet dated Sep. 9, 2015; with English machine translation (3 pages).
Confidential delivery bill from ASF to Euro Pépinières dated Sep. 14, 2015; with English machine translation (3 pages).
Redacted contract between ASF and Bonnet dated Sep. 22, 2015; with English machine translation (9 pages).
France plant application for NECTAKING dated Nov. 27, 2012; with English machine translation (2 pages).
European Community plant application for NECTAKING No. 2012/2702 dated Nov. 27, 2012; with English machine translation (2 pages).
European Community Official Gazette excerpt for NECTAKING dated Feb. 15, 2013; in English (12 pages).
Information sheet for NECTAKING dated Sep. 2015; with English machine translation (2 pages).
Information table for NECTAKING (Oct. 8, 2013); with English machine translation (5 pages).

* cited by examiner

*Primary Examiner* — Annette Para
(74) *Attorney, Agent, or Firm* — Westerman, Hattori, Daniels & Adrian, LLP

(57) ABSTRACT

A new and distinct variety of yellow nectarine tree denominated 'NECTAKING' has fruits with high eating quality and very long shelf life without alteration before and after harvesting, with a semi-sweet orange yellow flesh, with a slightly red pigmentation in a star shape around the stone cavity, and an attractive skin with a high percentage of dark red blush on skin surface, on a red background.

2 Drawing Sheets

Botanical designation: *Prunus persica* (L.) Batsch var. *nucipersica.*

Variety denomination: 'NECTAKING'.

BACKGROUND OF THE NEW VARIETY

The present invention relates to a new and distinct variety of yellow nectarine tree, *Prunus persica* (L.) Batsch var. *nucipersica*, which has been given the variety denomination 'NECTAKING'.

This new tree produces fruits with a long shelf life without alteration both on the tree after growth completion and after harvesting, very good eating quality, clingstone orange yellow flesh fruits, with a slightly red pigmentation in a star shape around the stone cavity, for fresh market in mid-July in the Pyrénées-Orientales department, France.

ORIGIN OF THE VARIETY

The 'NECTAKING' yellow nectarine tree originated from a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year, and are mostly found in Spring and Autumn. In May and October, very intense precipitations occasionally happen. Summer is dry with a few thunderstorms.

The 'NECTAKING' variety results from an open pollination using the 'NECTAGALA' variety (U.S. Plant Pat. No. 17,581) as the seed parent.

'NECTAKING' was provisionally designated, tested and genetically identified by a genetic profile, under number 4S.10W.44.08.

The 'NECTAKING' variety was obtained by hybridizing and propagated by grafting on an "INRA® GF677" rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety 'NECTAKING' yellow nectarine tree blooms at the end of February or during the first two weeks of March near Elne in the Pyrénées-Orientales department, France. The blooming period is considered medium. However, it was observed that its late date of blooming seems to be highly dependant on climatic conditions.

The first fruit of 'NECTAKING' ripens generally mid-July or at the end of July. The time of maturity for consumption is considered medium. However, it was observed that its date of maturity seems to be highly dependent on climatic conditions.

DESCRIPTION OF THE DRAWINGS

In the accompanying drawing, which are as nearly true as it is reasonably possible to make in a color illustration of this type.

Figure 1:
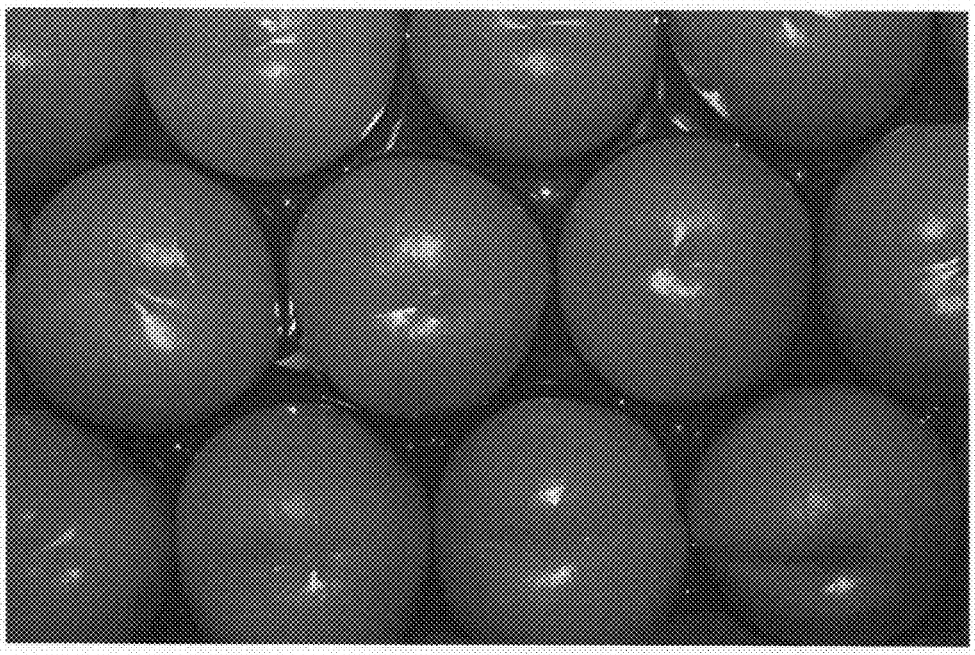
FIG. 1 is a color photograph that shows a close view of typical specimens of the fruits of the new variety 'NECTAKING' at ripening time.
Figure 2:
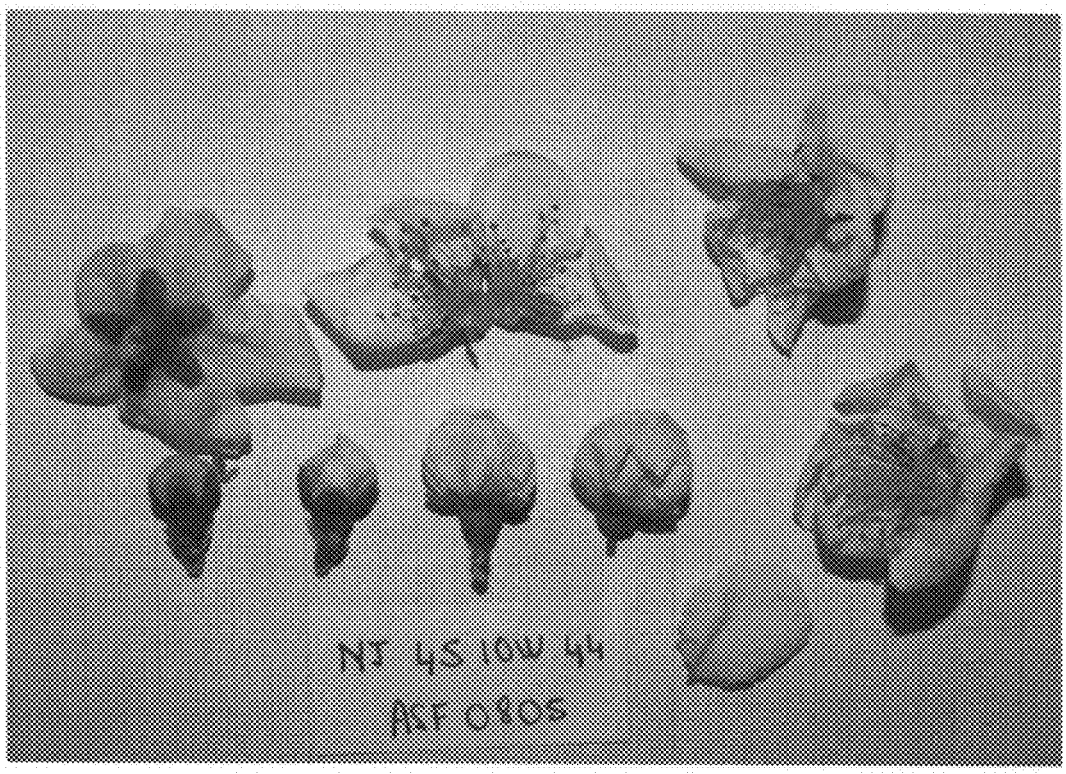
FIG. 2 is a color photograph which depicts the flower buds at different development stages, and the reverse and side view of the flower, and the reproductive organs with petals removed, of the new variety.
Figure 3:
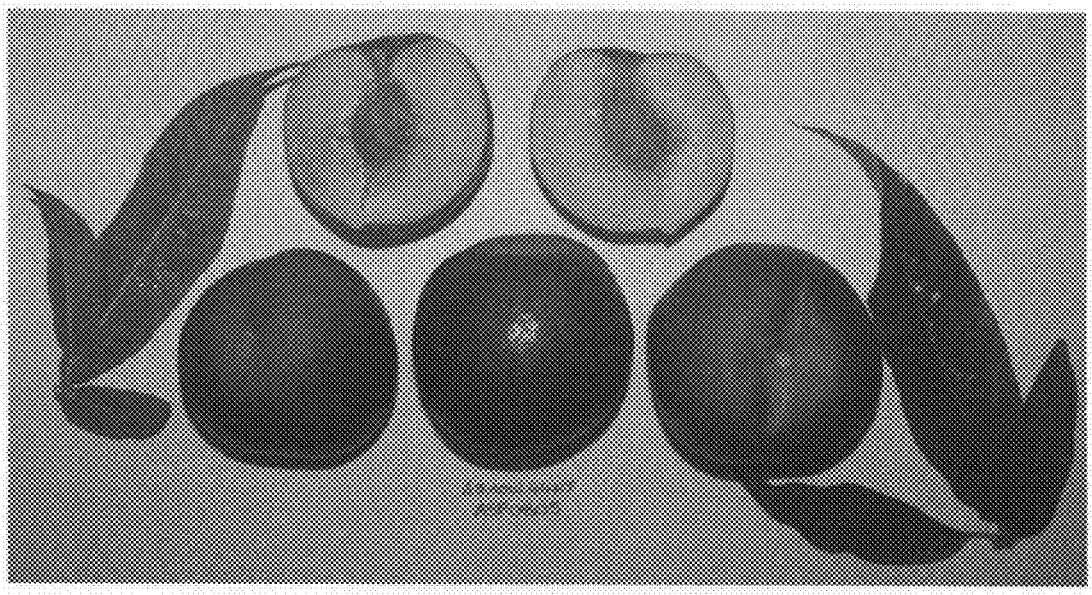
FIG. 3 is a color photograph which shows four typical specimens of the fruit, one of them having been cut in half with the pit being left in one of the halves for depicting leaves, fruit flesh, pit and pit cavity of the new variety.
Figure 4:
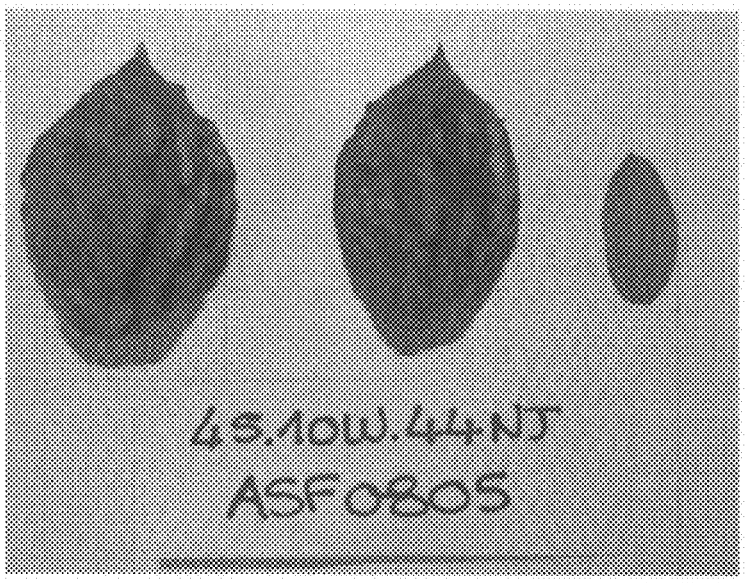
FIG. 4 is a color photograph showing different views of the stone of the new variety and the kernel of the stone.

Due to chemical development, processing and printing, the flowers, stones and fruits depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruits by 'NECTAKING' is high, due to fruit very long shelf life without alteration after harvesting.

Trees are vigorous and large stature half-standing in a semi-flared to semi-upright out aspect. The anthocyanic coloration of flowering shoot is present excluding brushwood side away from sun. The time of beginning of flowering is considered medium. More particularly, the flowering begins generally at the end of February or during the first two weeks of March. The type of flower is showy with medium petal size. Petals are medium pink. Leaf glands are present and reniform. The fruit flesh is orange yellow generally with a slightly red pigmentation in a star shape around the stone cavity. The fruit skin is very thick, with an homogenous dark red blush on a purple red background. The stone is clingstone and his size is medium. Fruit taste is semi-sweet, very aromatic and with a high level of sugars.

Compared to 'NECTARIANE' variety (U.S. Plant Pat. No. 17,707), 'NECTAKING' variety blooms 3 days earlier and the fruits of 'NECTAKING' variety ripen 7 days earlier than 'NECTARIANE' fruits. The maturity of 'NECTAKING' variety is considered medium. The fruits color of the new 'NECTAKING' variety is dark red on a purple red background, whereas 'NECTARIANE' fruits are colored in a bright red on 95 to 100 percent of the skin. Moreover, the 'NECTARIANE' fruits form is round and slightly elevated whereas 'NECTAKING' fruit form is round.

Compared to 'NECTAGALA' (U.S. Plant Pat. No. 17,581) variety, which is the female parent, 'NECTAKING' variety blooms 4 days earlier. Moreover, the fruits of 'NECTAKING' variety ripen approximately 1 month earlier than the fruits of 'NECTAGALA'. The fruits color of the new 'NECTAKING' variety is dark red on a purple red background. On the contrary 'NECTARIANE' fruits are colored in a bright red covering 80 percent of the fruits skin on an orange red background. Moreover, the 'NECTAGALA' fruits form is round to slightly oblong, whereas 'NECTAKING' fruit's form is round.

DETAILED DESCRIPTION

Referring more specifically to the pomological details of this new and distinct variety of yellow nectarine tree, the following was observed on trees in their third growing season (second year of production) under the ecological conditions prevailing at the orchards located near the town of Elne, Pyrénées-Orientales departement, France. All observations have been done on rootstock cultivars. Used rootstocks were "INRA® GF677" trees. All major color code designations are by reference to The R.H.S. Color Chart (Fourth Edition) provided by The Royal Horticultural Society of Great Britain.

Tree:

*Size*.—Generally. — Considered large. The tree size the first year was approximately 250 cm. The tree was pruned during each following dormant season to a height of approximately 250 cm. Current season shoots growth could reach 60 to 80 cm. The tree size from the second year (second and next years) reached a final height between 310 and 330 cm including current season shoots length. The tree size is consistently reduces to 250 cm the next years.

*Spread*.—Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

*Vigor*.—Considered strong.

*Productivity*.—Very productive and regular, every year. Fruit set is spaced by thinning to develop the remaining fruit into the desired market sized fruit. The number of the fruit set varies with the prevailing climatic conditions and cultural practices employed during the bloom period, and is therefore not distinctive of the present variety.

*Bearer*.—Very regular. The fruit distribution is considered homogenous on mixed branches. Thinning of 1 fruits out of 3 was necessary for the tree valorisation. Thinning was necessary every year during the years of observation.

*Form*.—The 'NECTAKING' variety has naturally a semi-flared to semi-upright shape.

*Hardiness*.—The present tree was grown and evaluated in France. The variety appears to be hardy under the central Pyrénées-Orientales departement typical climatic conditions. Experimentations on different sites with winter chilling requirement comprised between 350 hours and 1200 hours showed a good behaviour of the tree in all cases. No damages were caused by ascertained temperatures as low as −12 degrees Celsius in winter. The tree was also very resistant to frosty springtime weather.

Trunk:

*Diameter*.—Approximately between 5.5 and 6.5 centimeters in diameter when measured at a distance of approximately 30.0 centimeters above the soil level.

*Bark texture*.—Considered rough, with lenticels.

*Lenticels*.—Numerous lenticels are present. The lenticels range in size from approximately 20.0 to 40.0 millimeters in width, and about 15.0 millimeters in height.

*Lenticel color*.—The outside of lenticels has a silver-grey color (RHS Grey 201 C), whereas the inside is considered brown (RHS Greyed Orange 166 B).

*Bark coloration*.—The bark has a silver-grey color (RHS Grey 201 C or RHS Black 202 C) that is slightly darker that the lenticels color.

Branches:

*Size*.—Mature branches and current season shoots are considered medium for the variety.

*Diameter*.—Average as compared to other nectarine varieties. The current season shoots have a diameter from 5.0 to 7.0 millimeters, and mature branches have a diameter from 12.0 to 18.0 millimeters.

*Surface texture*.—Average, wood which is several years old has no furrowed appearance.

*Crotch angles*.—Primary branches are considered variable, but the crotch angles are generally between 50.0 degrees and 60.0 degrees from the horizontal axis.

*Current season shoots*.—Internode length: Generally between 25.0 and 35.0 millimeters.

*Color of mature branches*.—Considered brown (RHS Grey Brown 199 A to RHS Grey Brown 199 B).

*Current seasons shoots*.—Color. — The color of new shoot tips is considered pale yellow-green (RHS Yellow Green 144 A to RHS Yellow Green 144 C) on lower part of new shoot tips, whereas the upper part is darker and colored in brown-purple to brown red (RHS Greyed Purple Group 187 A to RHS Greyed Purple Group 187 B or RHS Greyed Red 182 A), depending on the level on the tip.

Leaves:

*Size*.—Considered medium to large for the species. The ratio leaf length/leaf width is 3,43.

*Leaf length*.—Approximately 143.0 to 170.0 millimeters without leaf petiole. The medium length is about 157.3 millimeters.

*Leaf width*.—Approximately 40.0 to 51.0 millimeters. The medium width is 45.9 millimeters.

*Leaf base shape*.—Concave.

*Leaf form*.—Lanceolate.

*Leaf tip form*.—Acuminate.

*Leaf color*.—Upper leaf surface. — Green (RHS Green 139 A or RHS Yellow Green 147 A). Lower surface. — A lighter green (RHS Yellow Green 146 A or RHS Yellow Green 147 B) than the upper leaf surface color.

*Leaf texture*.—Smooth and glabrous.

*Leaf venation*.—Pinnately veined.

*Mid-vein*.—Color. — Light green, almost cream yellow (RHS Yellow Green 150 D). The color may evolve with maturity.

*Leaf margins*.—Slightly undulating.

*Form*.—Considered slightly dentate.

*Uniformity*.—Leaves are isolated or grouped by 2 or 3. In this last case, one leaf of normal size is found with one or two smaller leaves (at least 50% smaller).

*Leaf petioles*.—Size. — Considered medium. Length. — Between10.0 and 12.0 millimeters. Diameter. — About 2.0 millimeters.

*Petioles color*.—Upper petiole surface. — Light green (RHS Yellow Green 145 A). Lower surface. — Light green (RHS Yellow Green 145 B to RHS Yellow Green 145 C).

*Leaf glands*.—Size. — Considered medium. Their length is about 1.2 millimeters and their width is about 1.0 millimeter. Number. — Generally 2 glands per leaf. Type. — Reniform. Color. — On young leaves, leaf glands color is considered a light green (RHS Green 144 B to RHS Green 144 A). On older leaves, leaf glands color turns to a dark brown (RHS Grey Brown 199 A to RHS Grey Brown 199 B). Margins. — Smooth and regular.

*Leaf stipules*.—Generally. — No leaf stipules were observed. But as seen in the characteristic relative to the leaves uniformity, it is possible to find leaves by groups of 2 or 3, with a normal-size leaf and smaller ones.

Flowers:

*Flower buds*.—Generally. — At pre-floral stage of development, the floral buds are conic in form with a round tip. Their form is evolving until blooming, with variables dimensions. Just before blooming, floral buds are approximately 12.0 millimeters wide and approximately 20.0 millimeters long. Color. — This characteristic is dependent upon the proximity to bloom. At pre-floral stage of development, the bottom of the flowers buds, formed by the sepals, is of purple-brown color (RHS Greyed Purple 183 A to RHS Greyed Purple 183 D or RHS Grey Brown Group 199 A). The corolla, formed by the petals, is generally of pale pink color (RHS Red Purple 65 B or RHS Red Purple 69 C). Petals color shows an evolution until the end of flowering.

*Hardiness*.—The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom*.—The blooming time generally begins at the end of February or during the first two weeks of March. The first bloom was observed on Mar. 1, 2009.

*Blooming time*.—Considered medium in relative comparison to other commercial nectarine cultivars grown in the Pyrénées-Orientales departement, France. The date of full bloom is observed generally at the middle of the blooming period. The date of bloom varies slightly with climatic conditions and cultural practices. Thus the full bloom was observed from Mar. 1 until Mar. 15, 2009, then from Mar. 17 until Mar. 25, 2010, then from Feb. 26 until Mar. 11, 2011, then from Mar. 14 until Mar. 25, 2012, and then from Feb. 26 until Mar. 16, 2013.

*Duration of bloom*.—Between 9 to 19 days. This characteristic varies slightly with the prevailing climatic conditions.

*Flower type*.—The variety is considered to have a showy type flower.

*Flower size*.—Considered large. Flower diameter at full bloom is approximately 28.0 to 32.0 millimeters.

*Bloom quantity*.—Considered abundant, approximately 60 flowers per meter, with a good distribution and a high rate of fruit set.

*Flower bud frequency*.—Generally 2 flower buds appear per node, occasionally 1.

*Petal size*.—Generally. — Considered medium. Length: Generally about 20.0 millimeters. Width: Generally about 20.0 millimeters.

*Petal form*.—Round-shaped.

*Petal count*.—Generally 5.

*Petal texture*.—Smooth, soft and glabrous.

*Petal color*.—Both surfaces of the petal are colored with a medium Pink (RHS Red Purple 65 B to RHS Red Purple 65 D) when young, becoming slightly darker until the end of blooming.

*Fragrance*.—Sweet.

*Petal claw*.—Form. — The claw is considered to have a conical form, slightly round at the top. Length. — Approximately 5.0 to 6.0 millimeters. Width. — Approximately 4.0 millimeters. Color. — The color of the petal claw is usually darker than the petal color.

*Petal margins*.—Generally considered wavy.

*Petal apex*.—Generally. — The petal apices are generally wide dome shaped.

*Flower pedicel*.—Length. — Considered medium to large and having an average length of approximately 4.0 millimeters. Diameter. — Considered average, approximately 2.0 millimeters. Color. — Yellow Green (RHS Yellow Green N144 A to RHS Yellow Green N144 B).

*Calyx*.—Internal surface texture. — Smooth and glabrous. Color. — The inner surface of the calyx is golden orange mat (RHS Greyed Red 178 C to RHS Greyed Red 178 D). The outer surface of the calyx is considered of purple-brown color (RHS Greyed Purple 183 A to RHS Greyed Purple 183 D).

*Sepals*.—Surface texture. — The outer surface has a short, fine pubescent texture. Size. — Average. Form. — Oval. Color. — Both sides of sepals are colored with a matt Red (RHS Greyed Purple 183 A to RHS Greyed Purple 183 D or RHS Grey Brown Group 199 A).

*Average number of stamens per flower*.—Approximately 45 stamens per flower.

*Anthers*.—Generally. — Medium in length. Color. — At an early stage of maturity, anthers are colored with an orange yellow color (RHS Yellow Orange 16 A to RHS Yellow Orange 16 B). The color may evolve with maturity to turn in red or orange red color (RHS Greyed Purple Group 178 A).

*Pollen production*.—Pollen is abundant, and has a yellow color (Approximately RHS Yellow Orange 17 B or RHS Yellow Orange 17 C) which may evolve with maturity. The present variety is considered auto-fertile (self-pollinating).

*Filaments*.—Size. — Medium length, between 9.0 to 17.0 millimeters in length. Color: Considered pale pink (RHS Red Purple 62 C or RHS Red Purple 62 D). The color becomes darker during the blooming (RHS Red Purple 73 A to RHS Red Purple 73 B).

*Pistil*.—Number. — Usually 1. Generally. — Average in size. Length. — Approximately 17.0 to 19.0 millimeters including the ovary. Color. — Considered a very pale green (RHS Yellow Green Group 150 D). The color evolves during the blooming, becoming more light (RHS Yellow Green Group 151 D). Ovary. — The pubescent is absent.

Fruit:

*Maturity when described*.—Very firm in ripe conditions (shipping ripe).

*Date of first picking*.—Jul. 12, 2008.

*Date of last picking*.—The date of harvest varies slightly with the prevailing climatic conditions. The 'NECTAKING' variety has a medium date of picking, and a grouped maturity. The maturity is grouped within 6 to 13 days and the harvest is generally performed in two runs. Last known picking times carry on Jul. 12 to Jul. 20, 2008, then on Jul. 14 to Jul. 19, 2009, then on Jul. 28 to Aug. 6, 2010, then on Jul. 10 to Jul. 20, 2011, then on Jul. 18 to Jul. 30, 2012, and then on Jul. 18 to Jul. 30, 2013.

*Size*.—Generally. — Homogeneous in size. Considered large.

*Average cheek diameter*.—Approximately 71.0 to 74.0 millimeters.

*Average axial diameter*.—Approximately 68.0 to 73.0 millimeters.

*Typical weight*.—Generally between 200.0 and 230.0 grams. This characteristic is high dependent upon the prevailing cultural practices, and therefore is not particularly distinctive of the variety.

*Fruit form*.—Generally. — Round. The fruit is generally uniform in symmetry, viewed from the suture's plane.

*Suture*.—Fruit suture: Wide-mouthed and slightly marked, extending from the base to the apex. No apparent callousing or stitching exists along the suture line. Not pointed. Color. — The suture has generally a similar color to the whole fruit color, a dark red (RHS Greyed Purple N186 C or RHS Greyed Purple 187 A).

*Ventral surface*.—Form. — Smooth.

*Apex*.—Non-prominent, generally slightly depressed.

*Base*.—Semi-flared, shallow.

*Stem cavity*.—Average depth of the stem cavity is about 15.0 to 18.0 millimeters. Average width is about 13.0 to 15.0 millimeters.

*Fruit skin*.—Thickness. — Considered very thick and strong, and the adherence of skin to flesh is strong to medium, depending on the fruit maturity. Texture. — Glabrous. Taste. — Semi-sweet, aromatic, with a high level of sugars. Tendency to crack. — None observed. Color: Blush color. — This blush color is a dark red (RHS Greyed Purple N186 C or RHS Greyed Purple 187 A). The purple red blush covers 80% to 95% of the fruit skin surface. The percentage of the blush on the fruit skin surface can vary, and is generally dependant upon the prevailing conditions under which the fruit was grown. Ground color. — The ground color covers approximately 5 to 20% of the fruit skin surface, and is considered red (RHS Greyed Purple 187 B).

*Fruit stem*.—Size Medium in length, approximately 10.0 to 12.0 millimeters. Diameter: Approximately 4.0 millimeters. Color: Pale green (RHS Yellow Green N144 A or RHS Yellow Green N145 A).

*Flesh*.—Ripens. — Very homogenously, slowly. The flesh has a long shelf life. Texture. — Very firm, very dense, crunchy, melting, juicy at harvest maturity stage. Fibers. — Not fibrous. Aroma. — Pronounced. Eating quality. — Considered very good, aromatic and with a high level of sugars. Flavor. — Considered semi-sweet. The Brix is generally superior to 13 and acidity comprised between 6 and 9 meq/100 ml. Juice. — Very juicy at complete maturity, little acid, with a high level of sugar. Brix. — Generally 13 to 15 degrees. This characteristic varies slightly with the number of fruit per tree; prevailing cultural practices; and the surrounding climatic conditions. Flesh color. — Considered orange Yellow (RHS Yellow Orange 16 A to RHS Yellow Orange 16 B) usually a slightly red pigmentation (RHS Orange Red N 34 A) in a star shape on approximately 5.0 millimeters around the stone cavity.

Stone:

*Type*.—Clingstone, more or less adherent depending on the fruit maturity.

*Size*.—Considered medium. The stone size varies significantly depending upon the tree vigor, crop load and prevailing growing conditions.

*Length*.—Approximately 30.0 to 33.0 millimeters.

*Width*.—Approximately 21.0 to 23.0 millimeters.

*Diameter*.—Approximately 17.0 to 19.0 millimeters.

*Form*.—Elliptic.

*Base*.—Straight, light, slanting.

*Apex*.—Shape. — The stone apex is short, pointed.

*Stone cavity*.—Considered medium size, with an ovate-form and dimensions corresponding to the stone's dimensions.

*Stone surface*.—Surface texture. — The pit is transversely furrowed on its entire surface. Furrows are more pronounced toward the apex. The stone is pitted toward the base. Relief is prominent generally and present basally. Ridges. — The surface texture is generally characterized by more prominent ridges along the ventral edges and is more prominent at the apical tip.

*Ventral edge*.—Width. — Considered small to medium, and having a dimension of approximately 2.0 millimeters at mid-suture.

*Dorsal edge*.—Shape. — Grooved.

*Stone color*.—The color of the dry stone is generally considered light orange brown (RHS Greyed Orange 164 A or RHS Greyed Orange N170 B).

*Tendency to split*.—Splitting is very low or absent, depending on climatic conditions between blooming period and stone hardening.

*Kernel*.—Size. — The kernel is considered medium. Length. — Approximately 17.0 millimeters. Width. — Approximately 8.0 millimeters. Thickness. — Approximately 3.0 to 4.0 millimeters. Form. — Considered flattened and elliptic. Pellicle. — The pellicle of the kernel has a pubescence. Color. — The kernel skin is light orange brown colored (RHS Greyed Orange N167 A). The almond, which is the seed of the kernel, is white cream (RHS Orange White 159 D) and has a bitter tasting. The kernel and its embryo are mature at the time of fruit maturity.

Use: The subject variety 'NECTAKING' is considered to be a yellow nectarine tree of medium season of maturity, and which produces fruits that are considered firm, attractively colored with a dark purple red. Fruits have a semi-sweet taste and are excellent for uncooked consumption, crunchy or melting when at full maturity. Fruits have excellent gustative qualities. Due to their flesh quality, firmness and density, they can also be commercialized as $4^{th}$ range product (packed fruit or fruit in bags for example). And they are also useful for both local and very long distance shipping.

Keeping quality: Remarkable. Fruit have a slow maturation and a long shelf life both on the tree after growth completion and after harvesting without alteration. After growth completion, fruits are preserved more than one week. After harvest, fruits are well preserved more than 4 weeks at 2.0 degrees Celsius.

Shipping quality: Considered very good. The fruit of the new yellow nectarine variety showed minimal bruising of the flesh or skin damage after being subjected to normal harvesting and packing procedures. Its resistance to handling during harvest and packing and its long shelf life without alteration after harvest easily permit 3 to 4 weeks-shipping at 2 degrees Celsius.

Resistance to insects and disease: No particular susceptibilities were noted. The present variety is not very sensitive to powdery mildew, or conservation diseases and decay due to its thick and strong skin.

Although the new variety of nectarine tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

We claim:

1. A new and distinct variety of yellow nectarine tree as illustrated and described, characterized by fruits with high eating quality and very long shelf life without alteration before and after harvesting, with a semi-sweet orange yellow flesh, with a slightly red pigmentation in a star shape around the stone cavity, and an attractive skin with a high percentage of dark red blush on skin surface, on a red background.

* * * * *